(12) United States Patent
Wiedmann et al.

(10) Patent No.: US 9,198,629 B2
(45) Date of Patent: Dec. 1, 2015

(54) DUAL ENERGY IMAGING WITH BEAM BLOCKING DURING ENERGY TRANSITION

(75) Inventors: Uwe Wiedmann, Clifton Park, NY (US); Denis Perrillat-Amede, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 0 days.

(21) Appl. No.: 13/459,578

(22) Filed: Apr. 30, 2012

(65) Prior Publication Data

US 2012/0326031 A1 Dec. 27, 2012

(30) Foreign Application Priority Data

May 2, 2011 (FR) ...................... 11 53740

(51) Int. Cl.

| | | |
|---|---|---|
| *H01J 35/14* | (2006.01) | |
| *A61B 6/00* | (2006.01) | |
| *H01J 35/10* | (2006.01) | |
| *H01J 35/30* | (2006.01) | |
| *G21K 1/02* | (2006.01) | |

(52) U.S. Cl.
CPC .................. *A61B 6/482* (2013.01); *A61B 6/405* (2013.01); *A61B 6/542* (2013.01); *G21K 1/02* (2013.01); *H01J 35/10* (2013.01); *H01J 35/14* (2013.01); *H01J 35/305* (2013.01); *A61B 6/4035* (2013.01); *H01J 2235/086* (2013.01); *H01J 2235/166* (2013.01)

(58) Field of Classification Search
CPC ............... A61B 2019/4036; A61B 2019/4045; A61B 2019/4054; A61B 6/4021; A61N 2005/1074; A61N 2005/1094; A61N 2005/10; G01V 5/0041

USPC ........ 250/399; 378/16, 62, 65, 108, 114, 140, 378/145, 137, 142

See application file for complete search history.

(56) References Cited

U.S. PATENT DOCUMENTS

| | | | | |
|---|---|---|---|---|
| 2,942,126 | A | * | 6/1960 | Silbermann .................... 378/109 |
| 3,973,156 | A | | 8/1976 | Schreiber |
| 4,336,476 | A | | 6/1982 | Holland et al. |
| 4,392,235 | A | * | 7/1983 | Houston .......................... 378/10 |
| 4,719,645 | A | | 1/1988 | Yamabe et al. |
| 6,052,434 | A | * | 4/2000 | Toth et al. ...................... 378/143 |
| 6,560,315 | B1 | * | 5/2003 | Price et al. ...................... 378/144 |
| 7,012,989 | B2 | | 3/2006 | Holland et al. |
| 7,050,542 | B2 | * | 5/2006 | Bathe et al. .................... 378/142 |

(Continued)

FOREIGN PATENT DOCUMENTS

| | | |
|---|---|---|
| DE | 102009004186 A1 | 1/2010 |
| JP | 54023492 A | 2/1979 |

OTHER PUBLICATIONS

FR Search Report issued in priority FR Application 1153740 Date of Search Report Jan. 10, 2012 (3 Pages).

*Primary Examiner* — Brooke Purinton

(74) *Attorney, Agent, or Firm* — GE Global Patent Operation; Marc A. Vivenzio

(57) ABSTRACT

A medical imaging method comprising generating a radiation at a first energy level by a radiation source, generating a radiation at a second energy level different from the first energy level by the radiation source, emitting the generated radiations at an output of the radiation source towards a detector, and blocking or diverting the emitted radiations during at least one intermediate phase during which the radiation source switches in a transient way from one of the first energy level and the second energy level to the other of the first energy level and the second energy level.

14 Claims, 7 Drawing Sheets

(56) References Cited

U.S. PATENT DOCUMENTS

| | | | |
|---|---|---|---|
| 7,065,179 B2* | 6/2006 | Block et al. | 378/134 |
| 7,359,486 B2* | 4/2008 | Subraya et al. | 378/141 |
| 7,476,023 B1* | 1/2009 | Canfield et al. | 378/203 |
| 8,358,741 B2* | 1/2013 | Grasruck et al. | 378/137 |
| 2004/0116804 A1* | 6/2004 | Mostafavi | 600/428 |
| 2005/0084060 A1 | 4/2005 | Seppi et al. | |
| 2005/0163281 A1 | 7/2005 | Negle | |
| 2006/0002515 A1* | 1/2006 | Huber et al. | 378/137 |
| 2009/0289195 A1* | 11/2009 | Henstra | 250/396 R |
| 2010/0172475 A1* | 7/2010 | Behling | 378/137 |
| 2011/0038460 A1* | 2/2011 | Grasruck et al. | 378/138 |
| 2011/0222660 A1* | 9/2011 | Wang et al. | 378/65 |

* cited by examiner

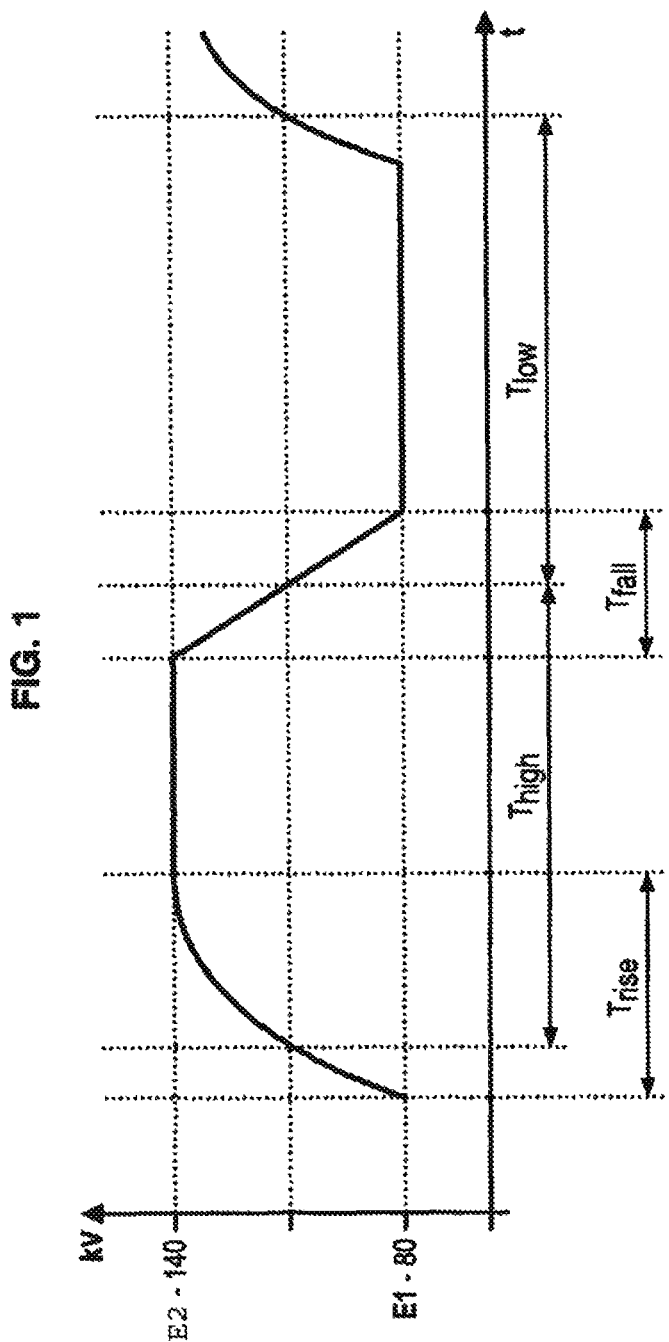

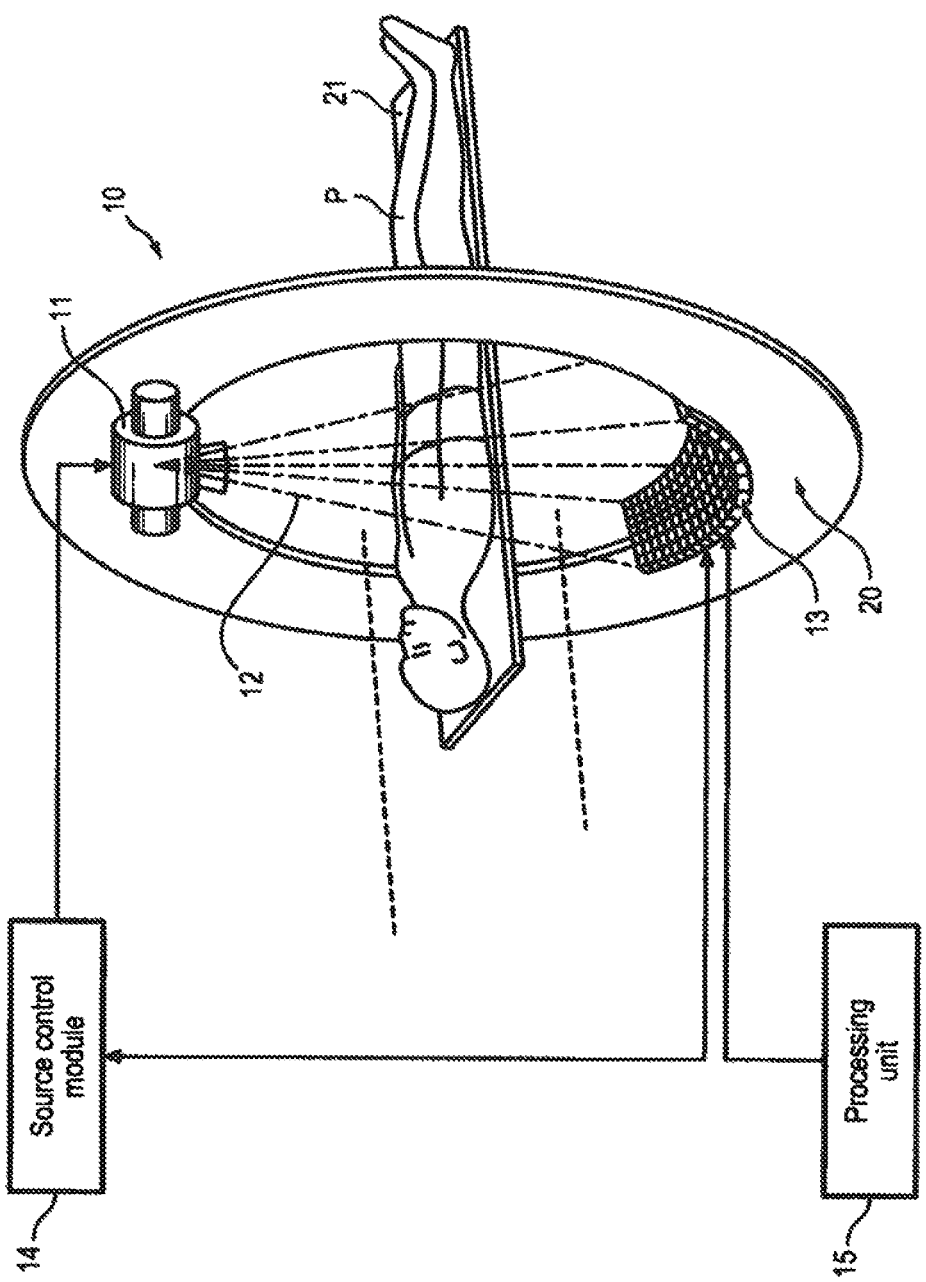

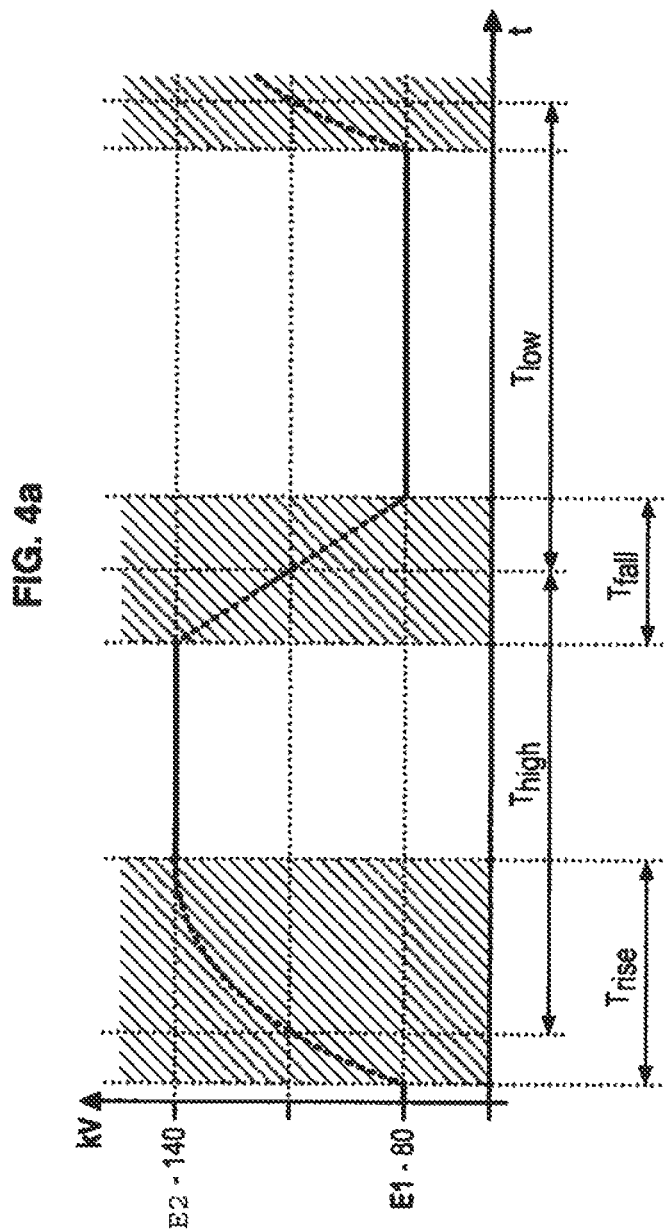

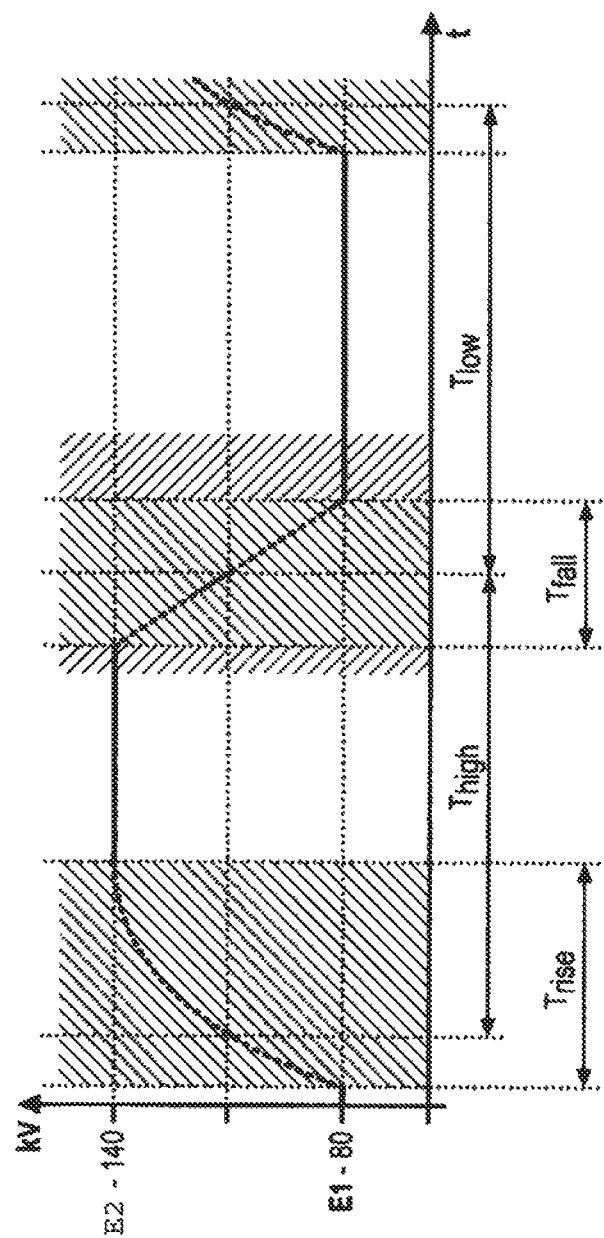

DUAL ENERGY IMAGING WITH BEAM BLOCKING DURING ENERGY TRANSITION

BACKGROUND OF THE INVENTION

1. Field of the Invention

Embodiments of the present invention generally relate to the field of medical imaging and the field of radiography. More particularly, embodiments of the present invention relate to dual-energy scanners.

2. Description of the Prior Art

Dual-energy scanners may be single-source scanners periodically emitting radiations with two different energies typically of the order of 80 kV and 140 kV respectively, and switching very rapidly from one to the other (of the order of about a thousand switches per revolution of the scanner, and from about 0.5 to about 5 revolutions per second).

As these radiations with different energies are not transmitted or reflected in the same way by organic tissues, notable enrichment of the information obtained in the final image, and an increase in its resolution may be achieved.

As shown in the graph of FIG. 1, which represents the energies of the emitted radiations versus time, these scanners nevertheless require transition times (called $T_{rise}$ and $T_{fall}$ in the figure) for switching from one energy to the other and vice versa, during which the energy is variable and distinct from the two "useful" energies E1 and E2 used for the imaging of a patient.

The emitted radiation doses during these transition times therefore only have a low interest for the image; furthermore, they provide an additional dose of radiations to the patient, whereas doses should be minimized in order not to be dangerous for the health of the patient.

Efforts have already been made for limiting the transition time between the useful energies, but there remains a phase during which the patient receives an unnecessary dose.

Furthermore, reducing the transition time complicates the structure of the electronic circuit used in the scanner and makes the latter heavier.

Therefore, there exists a need for a novel technique with which images may be produced from radiations with two different energies without these images being altered by additional radiations of non-useful energies, and in which the doses of non-useful radiations absorbed by the patient are limited.

Methods for applying sources of radiations have already been developed with which all or part of the radiations may be prevented from attaining a patient, in order to modulate the dose received by this patient.

To achieve this, radiation sources of the type comprising a source of electrons and a target, adapted so as to emit a flux of X-rays towards a patient or an area of the patient to be imaged when it receives a flux of electrons, are used.

The source further comprises a system for deflecting the flux of electrons, which modifies the path of the electron flux so that it attains another point of the target and the dose sent towards the patient is modified.

However, with such a device, it is only possible to achieve dose modulation, but not to mask certain energies at given time intervals; the obtained result is therefore not satisfactory.

BRIEF SUMMARY OF THE INVENTION

According to an embodiment of the present invention, there is provided a medical imaging method. The method comprises generating a radiation at a first energy level by a radiation source, generating a radiation at a second energy level different from the first energy level by the radiation source, emitting the generated radiations at an output of the radiation source towards a detector, and blocking or diverting the emitted radiations during at least one intermediate phase during which the radiation source switches in a transient way from one of the first energy level and the second energy level to the other of the first energy level and the second energy level.

According to another embodiment of the present invention, there is provided a medical imaging device. The device comprises a source of radiations, a detector of radiations, and a control module configured to control the source of radiations to generate a radiation at a first energy level, to generate a radiation at a second energy level different from the first energy level, and to emit the generated radiations at an output of the source of radiations towards the detector of radiations, wherein the emitted radiations are blocked or diverted during at least one intermediate phase during which the source of radiations switches in a transient way from one of the first and second energy levels to the other of the first and second energy levels.

BRIEF DESCRIPTION OF THE DRAWINGS

Embodiments of the present invention will be more apparent to those skilled in the art upon reading the following description with reference to the accompanying drawings, in which:

FIG. 1 illustrates the time-dependent change in the energies emitted in a dual-energy tomograph;

FIG. 2 illustrates an exemplary medical imaging device applying a method according to an embodiment of the present invention;

FIG. 4a illustrates the time-dependent change in the emitted energies in a dual-energy tomograph with blocking of the radiations in the intermediate phases according to an embodiment of the present invention;

FIG. 4b illustrates the time-dependent change in the emitted energies in a dual-energy tomograph with blocking of the radiations in the intermediate phases and dose modulation according to an embodiment of the present invention.

DETAILED DESCRIPTION OF THE INVENTION

Figure 3A:
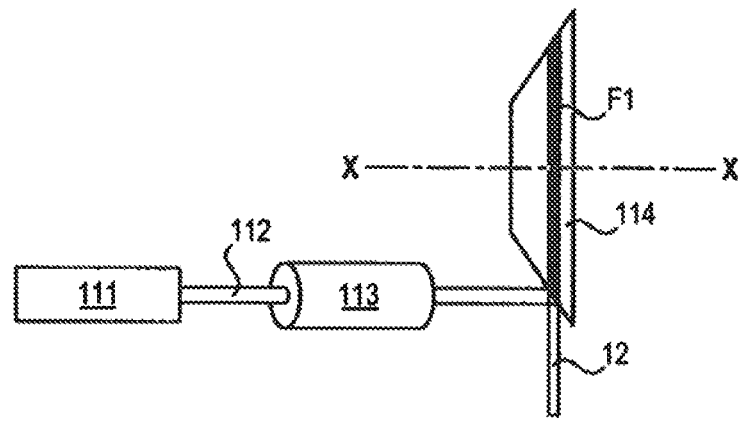
FIG. 3a schematically illustrates a source of radiations used in a medical imaging device according to an embodiment of the present invention.

With reference to FIG. 2, a tomography device 10 comprising a source of radiations 11 and a detector of radiations 13, positioned on a rotating support 20 is illustrated. The source of radiations 11 emits a beam of radiations 12, for example X-rays, towards the detector 13 and through a patient P, or an area of a patient P to be imaged, lying on a support 21.

When the detector 13 receives the radiations 12, with a processing unit 15 connected to the detector 13, it is possible to store the images obtained by the detector 13 and optionally perform additional processing on these images, in order to, for example, reconstruct a 3D image of the area of the patient P to be imaged.

Further, the tomography device 10 comprises a module 14 for controlling the source 11, which is connected to the source 11 and in particular controls the dose and the energy of the radiations 12 emitted by the source 11 towards the patient P.

In the case of a dual-energy tomography device, the source 11 should only emit towards the patient P, radiations with two distinct energy levels E1 and E2 useful for forming the image. The moments during which the transitions between both of these energy levels have to be made depend on the angular position of the rotating support 20. The rotating support 20 at these moments sends to the control module 14 the order to modify the energy of the radiations, and the control module 14 modifies the energy of the source 11 according to these orders.

This control module 14 may also control the source 11 so that the latter only delivers towards the detector 13 and through the patient P, or an area of the patient P to be imaged, radiations with two distinct energy levels E1 and E2 useful for forming the image, and does not deliver transition energies between both of these energy levels.

Optionally, the control module 14 may, in order to control the dose of the radiations emitted towards the patient P, also be connected to the detector 13 and use information on the radiation dose received by the detector 13 in order to adapt the dose of radiations 12 emitted by the source 11.

Figure 3B:
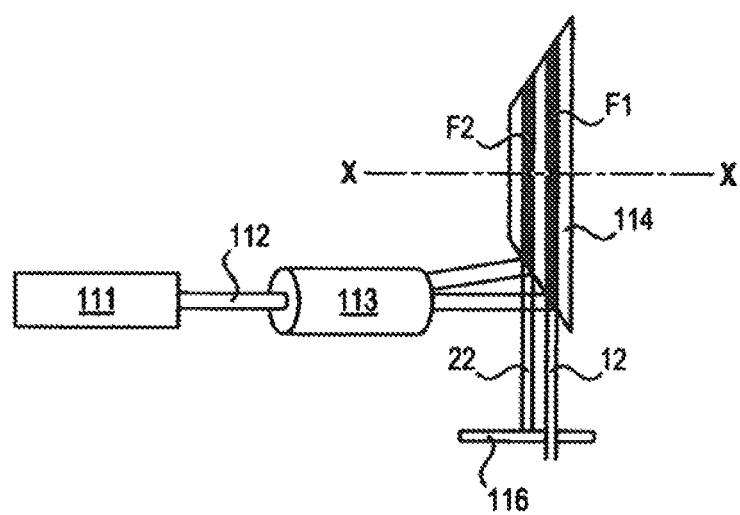
FIG. 3b illustrates a source of radiations used in a medical imaging device according to an embodiment of the present invention.

The source of radiations 11 is illustrated in more detail in FIGS. 3a-3b. It comprises a source of electrons 111 and an anode or target 114 which emits radiation, for example of the X-ray type, when it receives a flux of electrons 112.

The target 114, illustrated in FIG. 3a, comprises a first focal area F1 adapted so as to emit the radiation 12 towards the detector 13 through the patient P when it receives the flux of electrons 112 emitted by the source of electrons 111.

The target 114 may also comprise a second focal area F2, illustrated in FIG. 3b, which, when it receives all or part of the flux of electrons 112 emitted by the electron source 111, may emit a beam of radiations 22 which is diverted or blocked so as not to be received by the patient P. Alternatively, the second focal area F2 may emit no radiation when it receives a flux of electrons.

Finally, the source of radiations 11 comprises a deflection system 113, positioned between the source of electrons 111 and the target 114, and which may modify the trajectory of the electron beam 112. This deflection may be achieved in any known way, for example by magnetic or electrostatic deflection.

During an examination of the patient P, the electron source 111 successively generates a flux of electrons 112 at a first energy level, at a second energy level distinct from the first energy level, and during intermediate phases at a variable energy level during the time for switching in a transient way from the first to the second energy level or vice versa. The energy levels are adapted so that the radiation emitted by the target 114 and resulting from this flux of electrons 112, has the profile illustrated in FIG. 1.

In particular, the resulting radiation 12 of this flux of electrons 112 successively has, over time, first and second energy levels E1 and E2 respectively, and intermediate phases $T_{rise}$ and $T_{fall}$, during which the energy level switches in a transient way from the first energy level E1 to the second energy level E2 or vice versa.

According to a first embodiment illustrated in FIG. 4a, the radiation source 11 is controlled so that during stationary phases, during which the energy level is constant or equal to E1 or E2, the flux of electrons 112 generated by the source of electrons 111 attains the focal area F1, so that the latter generates radiation 12 towards the detector 13 through the patient P.

On the other hand, during the intermediate phases $T_{rise}$ and $T_{fall}$, the radiation source 11 is controlled so that the flux of electrons 112 does not reach the focal area F1, and thus no radiation is generated in the direction of the patient P.

The intermediate phases $T_{rise}$ and $T_{fall}$, during which the energy of the electron flux 112 varies from a state E1 or E2 to the other state, and where no transient radiation is emitted towards the patient P, are shown as hatched lines in FIG. 4a.

With reference to FIG. 4b, the duration of the phase during which no radiation is emitted through the patient P may also be adapted in order to modulate the dose received by the latter.

Indeed, although it is possible to limit the duration of this phase to the intermediate phases $T_{rise}$ and $T_{fall}$, it is also possible to extend the blocking of the radiation before and after each of these phases, in particular in order to reduce the dose of radiations 12 received by the patient P.

These areas are also illustrated with hatchings in FIG. 4b.

In order to achieve this blocking of the radiations, or more generally to prevent the electron flux from reaching the focal area F1 of the target 114, several embodiments are possible.

Generally, the electron flux 112 may reach the first focal area F1 during the stationary phases, and be only diverted during the intermediate phases $T_{rise}$ and $T_{fall}$.

Alternatively, the flux of electrons 112 may only be diverted during the stationary phases so as to reach the first focal area F1, or further it may be diverted according to several different trajectories depending on whether one is in a stationary phase or an intermediate phase.

Furthermore, the way to prevent the electron beam 112 from reaching the focal area F1 during intermediate phases may also vary.

Figure 5A:
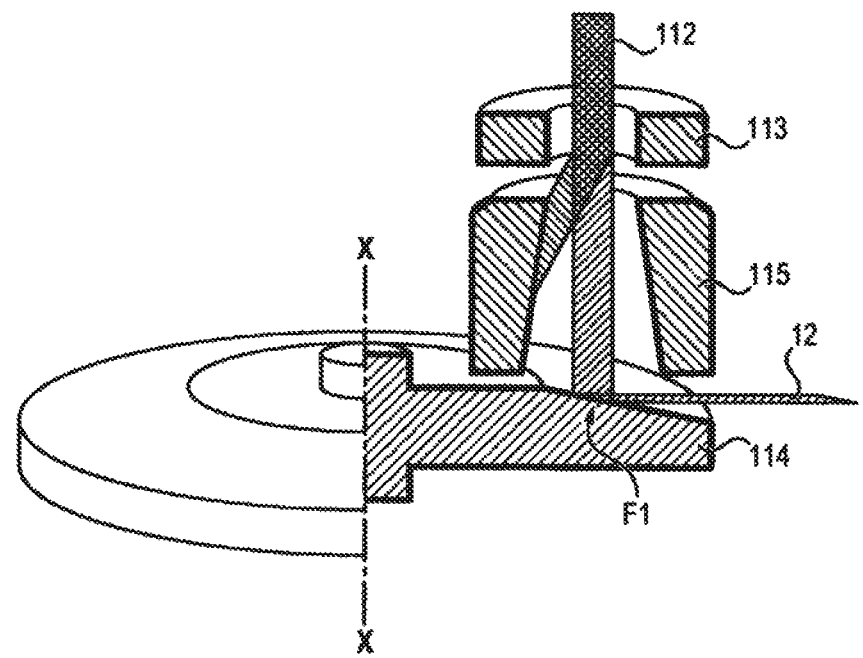
FIGS. 5a to 5d illustrate exemplary embodiments of an imaging method according to embodiments of the present invention.

According to an embodiment, with reference to FIG. 5a, the radiation source 111 may comprise an electron collector 115 positioned between the deflection system 113 and the target 114.

The deflection system 113 diverts the trajectory of the electron beam 112 onto the collector 115 so that this beam follows a circular trajectory onto the collector 115 for example. To do this, this electron collector 115 may be an axisymmetrical solid comprising a through-aperture through which passes the electron beams 112 during the stationary phases, in order to reach the focal area F1 of the target 114. For example, the collector 115 may be an axisymmetrical solid centered on the electron beam 112 during the stationary phases.

It may also have an inner surface delimiting the through-aperture through which passes the electron flow, and towards which is diverted the trajectory of the electron flux 112 during the intermediate phases.

The electron collector 115 may consist of a material such as copper, beryllium or ceramics of the alumina type ($Al_2O_3$), with which all or part of the electron flux may be absorbed without emitting any radiation, and further having good thermal properties such as good heat conduction, capacity and durability at high temperatures. Alternatively, the electron collector 115 may emit radiations and a collimator 116, positioned between the collector 115 and the patient P, may be adapted for blocking the radiations stemming from the collector 115 while transmitting the radiations stemming from the first focal area F1.

The geometry of the collector 115 in the form of an axisymmetrical solid is preferable since it allows the collector to be driven into rotation around its axis of revolution, which allows an increase in the surface area against which the electron flux is diverted, and thus any overheating of this surface may be avoided.

Figure 5B:
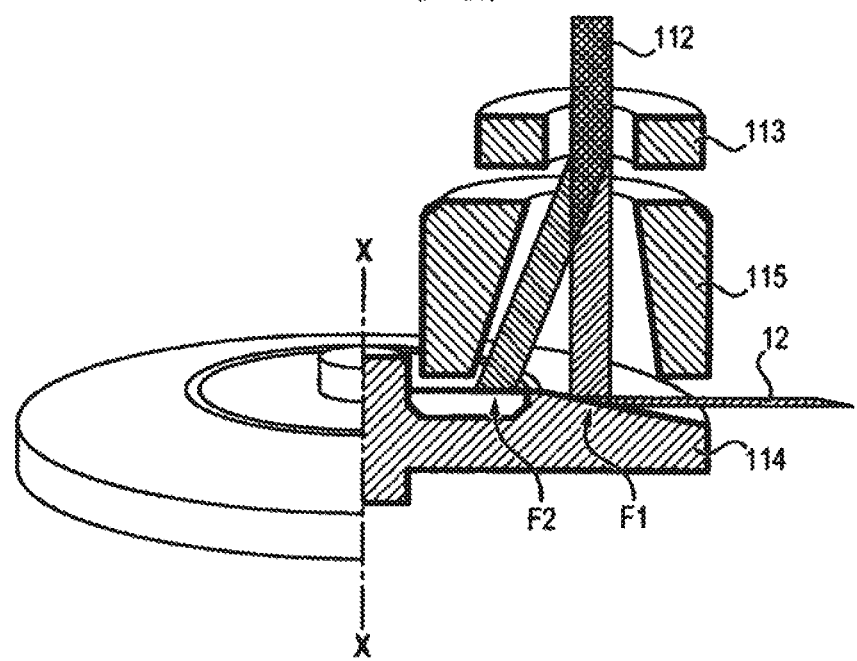
Figure 5C:
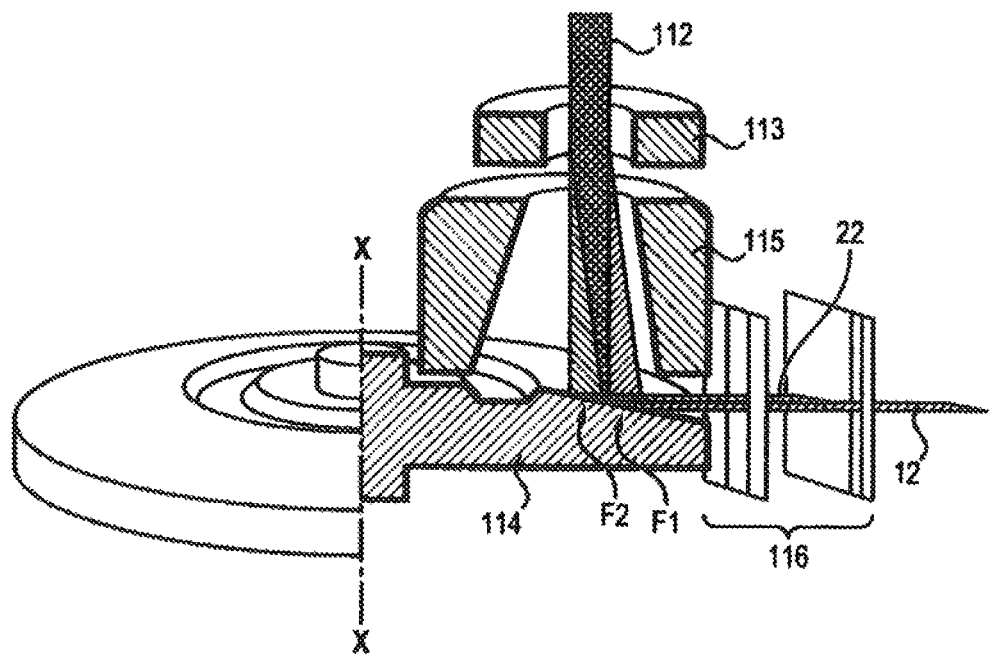
Figure 5D:
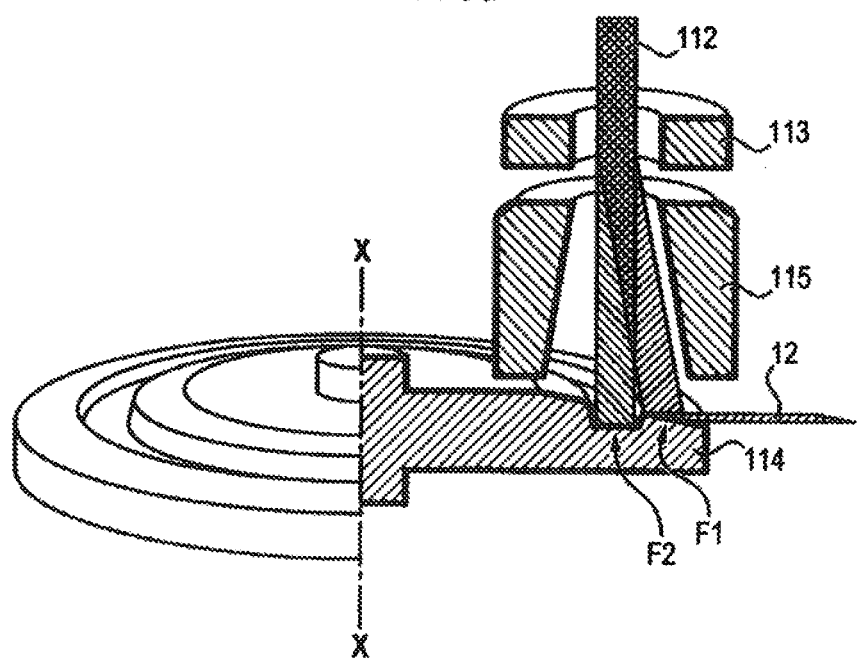

Alternatively, as illustrated in FIGS. 5b, 5c, and 5d, the electron beam 112 emitted during the intermediate phases may be diverted towards a second focal area F2 absorbing the electrons without emitting any radiation or emitting radiations towards a direction distinct from that of the patient P and of the detector 13.

The target 114 may have the shape of axisymmetrical solid with axis X-X, having a surface tilted relatively to the incident electron flow 112, and the focal areas F1 and F2 may be portions of the target 114 in the form of concentric and distinct rings distinct from the target 114. This allows the target 114 to be driven into rotation around its axis X-X and the surface area of the focal areas may thereby be increased in order to avoid their overheating when they are exposed to the electron flux.

Furthermore, it is also possible to defocus the electron beam 112 during the intermediate phases for limiting heating-up of the target 114.

According to an embodiment, as illustrated in FIG. 5b, the second focal area F2 may be a focal area consisting of a material such as copper, beryllium or ceramics of the alumina type ($Al_2O_3$). The second focal area F2 may be adapted for absorbing all or part of the electron flux 112 without emitting any radiation, and further more may have good thermal properties such as good heat conduction, heat capacity and durability at high temperature. A collimator 116 (not shown) positioned downstream from the source 111, if required, gives the possibility of only transmitting the radiations stemming from the first focal area F1. This collimator 116 may, for example, consist of at least two non-aligned windows, allowing limitation of the aperture transversely to the incident radiations, but also blocking of the radiations stemming from directions other than that of the first focal area F1.

According to an alternative embodiment illustrated in FIG. 5c, the focal area F2 may be adapted in order to emit radiation 22 towards a direction different from that of the detector 13 and of the patient P. To do this, the second focal area F2 may, for example, have a different tilt relatively to the incident flux 112 of electrons from that of the first focal area F1.

In this case, the radiation 22 is stopped by a collimator 116 positioned downstream from the target 114, and adapted for only letting through the radiation 12 stemming from the first focal area F1, and therefore for blocking radiations 22 stemming from the second focal area F2. This collimator 116 may then have a structure identical with the one shown earlier.

Alternatively, the second focal area F2 may be a groove made in the target 114, as illustrated in FIG. 5d, emitting radiation 22 which is in majority confined in the groove. To do this, the groove may be positioned so that the radiation 22 is emitted towards a wall of the groove (not shown in the figures) and not towards the outside of the groove. Nevertheless, a small proportion of the radiations may be emitted outwards, so as to be blocked by the collimator 116 in the same way as earlier, since it is not emitted in the same direction as the first focal area F1.

Finally, during the whole duration of exposure of the patient P, the control module 14 of the source 11 measures the radiation doses received by the detector 13 and therefore by the patient P. From these measurements, it may order the source 11 to block or to divert the radiations according to the embodiments described above, in order to limit the dose received by the patient P depending on a dose level per image to which the patient P may be subject.

Thus in every case, during the intermediate phases $T_{rise}$ and $T_{fall}$, during which the energy of the radiations is variable over time, no radiation reaches the patient P or the detector 13, so that the patient P is not subject to too large of a dose and the detector 13 does not receive any parasitic radiation which may deteriorate the quality of the image obtained.

What is claimed is:

1. A medical imaging method, comprising:
generating an electron beam at one of a first energy level and a second energy level by an electron source, the second energy level being different from the first energy level;
emitting radiation from a target through a patient and towards a detector upon receiving the electron beam at the target; and
blocking or diverting the electron beam prior to reaching the target during at least one intermediate phase during which the electron source switches in a transient way from one of the first energy level and the second energy level to the other of the first energy level and the second energy level,
wherein:
the electron source comprises a deflection system and an electron collector positioned between the electron source and the target,
the electron collector defines an aperture through which the electron beam passes, and comprises an inner surface, wherein at least a portion of the inner surface is tilted so that the cross section of the aperture changes along a path of the electron beam, and
the step of blocking or diverting the electron beam comprises deflecting the electron beam toward the inner surface of the electron collector.

2. The method according to claim 1, further comprising:
modulating the duration of the at least one intermediate phase during which the electron beam is blocked or diverted depending on a dose level per image to which a patient may be subjected.

3. The method according to claim 1, wherein the electron source comprises:
a source of electrons configured to emit a flux of electrons; and
the target comprising a first focal area, through which the radiation is emitted when the first focal area is exposed to the flux of electrons, the flux of electrons being diverted relative to the first focal area during the at least one intermediate phase.

4. The method according to claim 3, wherein the flux of electrons is blocked or diverted by magnetic deflection or electrostatic deflection.

5. A medical imaging device, comprising:
an electron source;
an X-ray detector;
the electron source being controlled by a control module to generate an electron beam at one of a first energy level, and a second energy level different from the first energy level, and to emit the electron beam towards the X-ray detector, the electron source generating an electron beam of variable energy over time during an intermediate phase during which the electron source switches in a transient way from the first energy level to the second energy level or vice versa; a target comprising a focal area adapted to emit X-rays towards the detector through a patient upon receiving the electron beam;
the electron source further comprising:
a deflection system positioned between the electron source and the target, adapted so as to modify the trajectory of the electron beam during the intermediate phase
an electron collector positioned between the deflection system and the target, the electron collector defining an aperture through which the electron beam passes, and comprising an inner surface, wherein at least a portion of the inner surface is tilted so that the cross section of the aperture changes along a path of the electron beam, and the deflection system configured to divert the electron beam towards the inner surface of the electron collector during the intermediate phase.

6. The medical imaging device according to claim 5, wherein said electron collector is adapted for absorbing the electron beam.

7. The medical imaging device according to claim 5, wherein the target further comprises at least one second focal area through which X-rays are not emitted when the at least one second focal area is exposed to a flux of electrons, and wherein the flux of electrons is diverted by the deflection system towards the at least one second focal area during the at least one intermediate phase.

8. The medical imaging device according to claim 7, wherein the at least one second focal area is configured to absorb the flux of electrons.

9. The medical imaging device according to claim 5, wherein the target further comprises at least one second focal area through which radiations are emitted towards a direction distinct from a direction of emission of the first focal area, the medical imaging device further comprising a collimator positioned between the target and the detector, wherein the collimator is configured to block the radiations emitted from the at least one second focal area.

10. The medical imaging device according to claim 8, wherein the target is an axisymmetrical solid centered on an axis, wherein the target rotates around the axis, and wherein the first focal area and the at least one second focal area are concentric rings distinct from each other.

11. The medical imaging device according to claim 10, wherein the at least one second focal area is a groove in the target, wherein the electron beam emitted towards the at least one second focal area is blocked by a wall of the groove.

12. The medical imaging device according to claim 5, further comprising a processing unit configured to process images obtained by the detector.

13. The medical imaging device according to claim 7, wherein the at least one second focal area is on the inner surface.

14. The medical imaging device according to claim 8, wherein the at least one second focal area is on the inner surface.

* * * * *